United States Patent
Garcia et al.

(10) Patent No.: US 8,591,066 B2
(45) Date of Patent: Nov. 26, 2013

(54) MODULAR LAMP HEAD AND ASSEMBLY FOR NON-DESTRUCTIVE TESTING

(75) Inventors: Gustavo Garcia, East Setauket, NY (US); John Duerr, Massapequa Park, NY (US); Chih-Tsung Su, Hsin-Chaung (TW)

(73) Assignee: Spectronics Corporation, Westbury, NY (US)

( * ) Notice: Subject to any disclaimer, the term of this patent is extended or adjusted under 35 U.S.C. 154(b) by 711 days.

(21) Appl. No.: 12/583,218

(22) Filed: Aug. 17, 2009

(65) Prior Publication Data
US 2010/0044589 A1   Feb. 25, 2010

Related U.S. Application Data

(60) Provisional application No. 61/189,397, filed on Aug. 19, 2008, provisional application No. 61/203,037, filed on Dec. 17, 2008.

(51) Int. Cl.
*F21V 29/00* (2006.01)

(52) U.S. Cl.
USPC . 362/294; 362/231; 362/249.02; 362/249.03; 362/373; 362/96; 362/218; 361/679.52; 361/697; 361/704; 361/709; 361/712; 165/80.2; 165/80.3; 165/104.33; 165/185; 454/184

(58) Field of Classification Search
USPC ......... 362/231, 249.02, 249.03, 294, 373, 96; 362/218; 361/679.46–679.52, 690–697; 361/704–712; 165/80.2, 80.3, 104.33, 185; 454/184
See application file for complete search history.

(56) References Cited

U.S. PATENT DOCUMENTS

| | | | |
|---|---|---|---|
| 5,788,364 A * | 8/1998 | Cooper et al. | 362/293 |
| 6,767,110 B2 | 7/2004 | Cooper et al. | |
| 7,344,272 B2 | 3/2008 | Cooper et al. | |
| 7,559,676 B2 * | 7/2009 | Rasmussen et al. | 362/264 |
| 2003/0086271 A1 * | 5/2003 | Masuoka et al. | 362/345 |
| 2003/0137838 A1 * | 7/2003 | Rizkin et al. | 362/240 |
| 2004/0075400 A1 * | 4/2004 | Su | 315/291 |
| 2004/0223342 A1 * | 11/2004 | Klipstein et al. | 362/555 |
| 2006/0262544 A1 * | 11/2006 | Piepgras et al. | 362/373 |
| 2007/0285926 A1 * | 12/2007 | Maxik | 362/294 |
| 2008/0013316 A1 * | 1/2008 | Chiang | 362/264 |

OTHER PUBLICATIONS

Track Lighting Accessories, Wen Hui Enterprise Co., Ltd., 1 page, http://www.cens.com/ishow/w/wenhui/pro3.htm (dated prior to Aug. 17, 2009.).

* cited by examiner

*Primary Examiner* — Robert May
*Assistant Examiner* — Tsion Tumebo
(74) *Attorney, Agent, or Firm* — Drinker Biddle & Reath LLP

(57) ABSTRACT

A lamp module for use in non-destructive testing and inspection. The module including a module body with a front and rear end, and a side wall. The module body includes a mounting chamber located within the side walls. A plurality of LEDs are mounted within the chamber and oriented to so as to emit light out of the front end of the body. At least one LED emits light having a wavelength selected to produce fluorescence of an illuminated material. A fan is mounted to the body to dissipate heat generated by the LEDs when the fan is activated. Electrical connectors extend out of the body and are electrically connected to the LEDs and the fan for supplying current. The module can be installed in various structures or systems, including in a luminaire, an overhead light housing or a track light system.

22 Claims, 8 Drawing Sheets

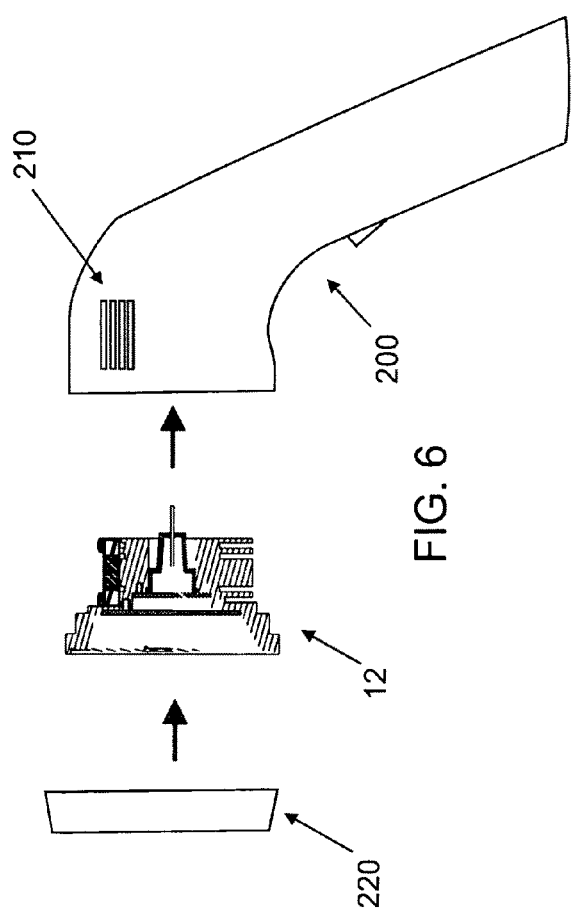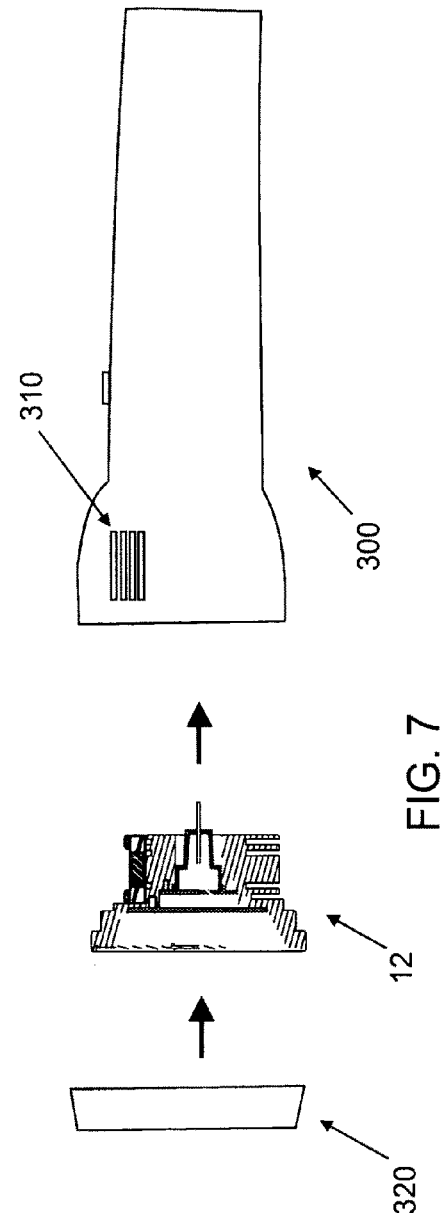

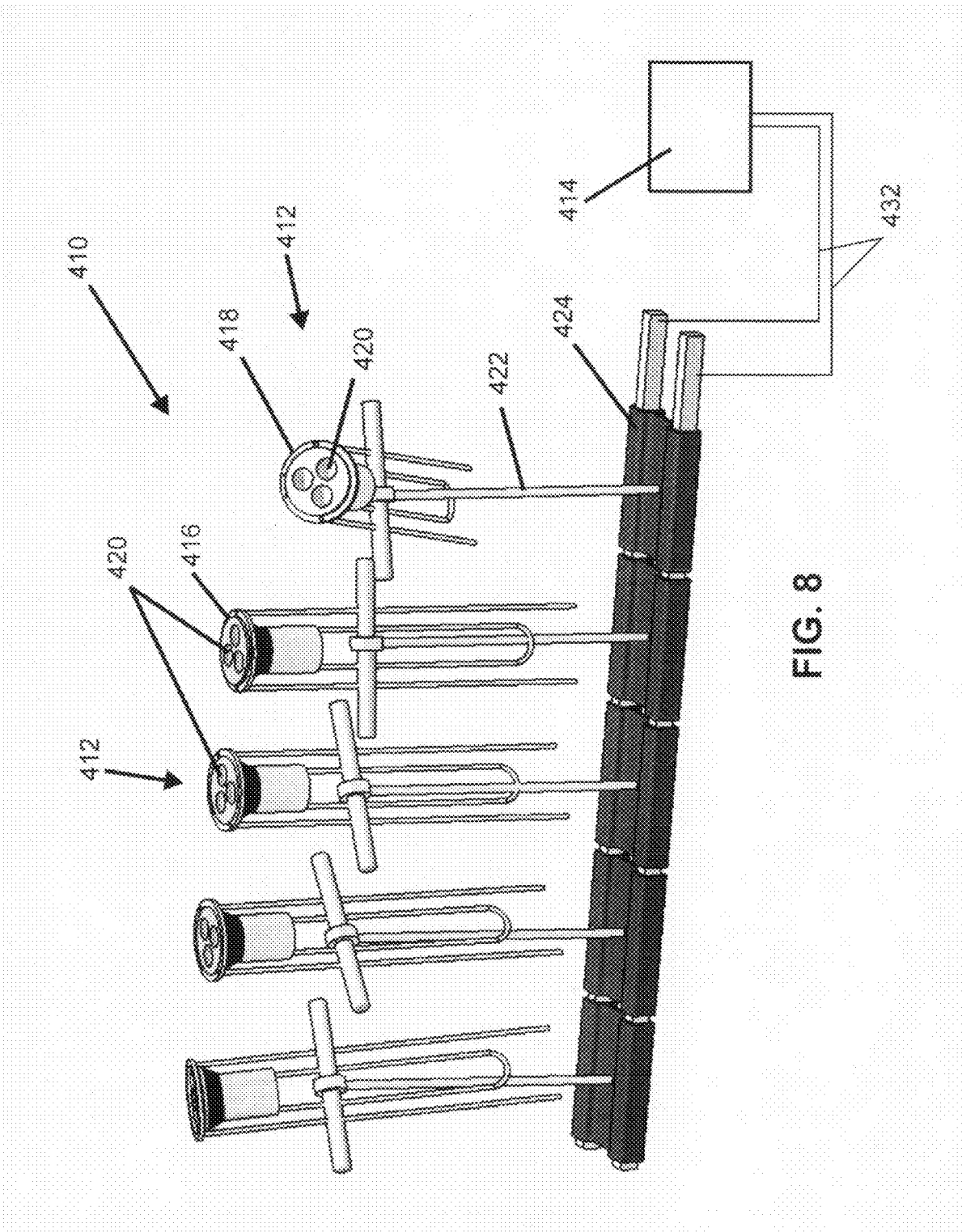

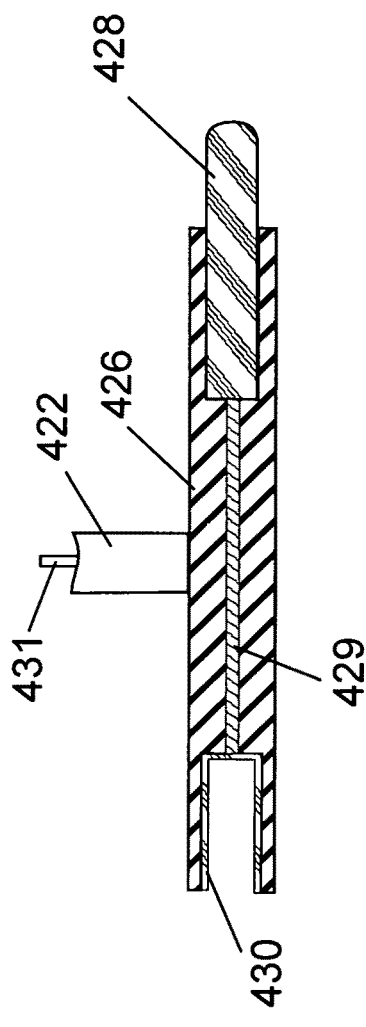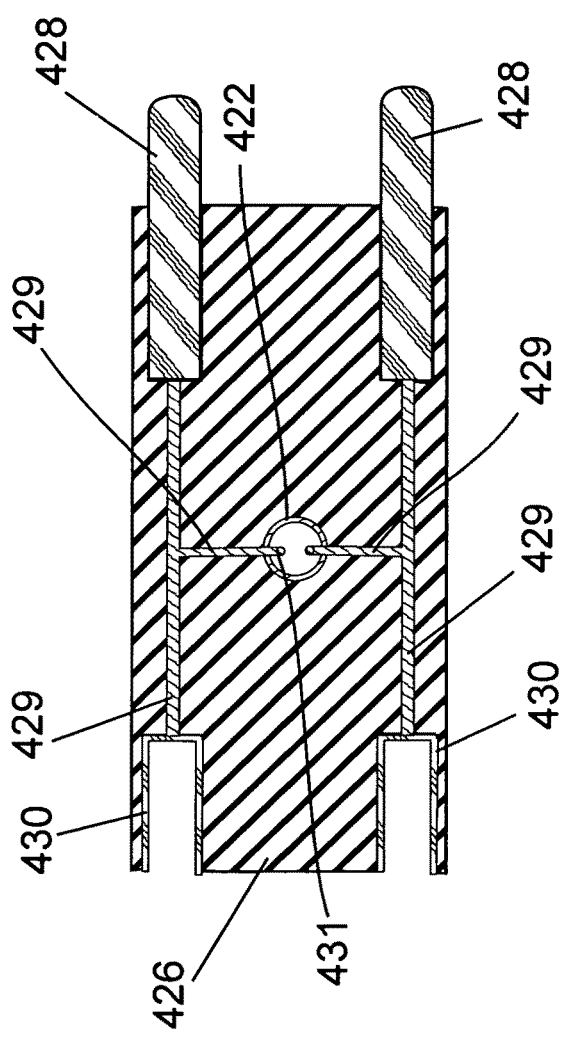

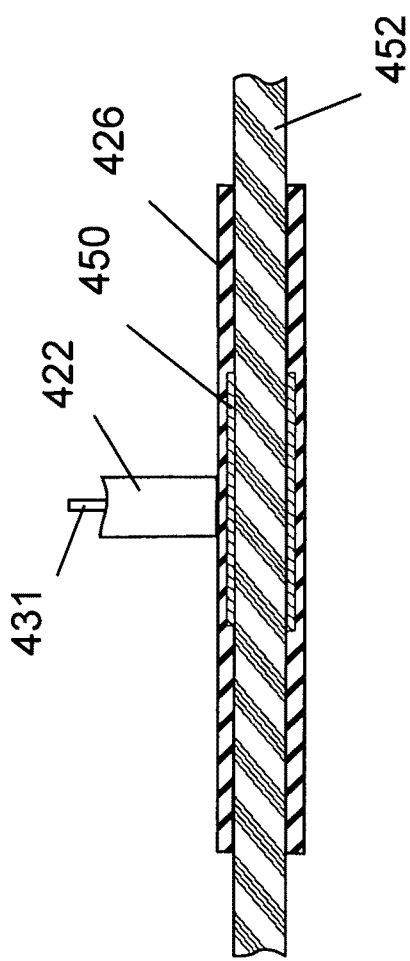
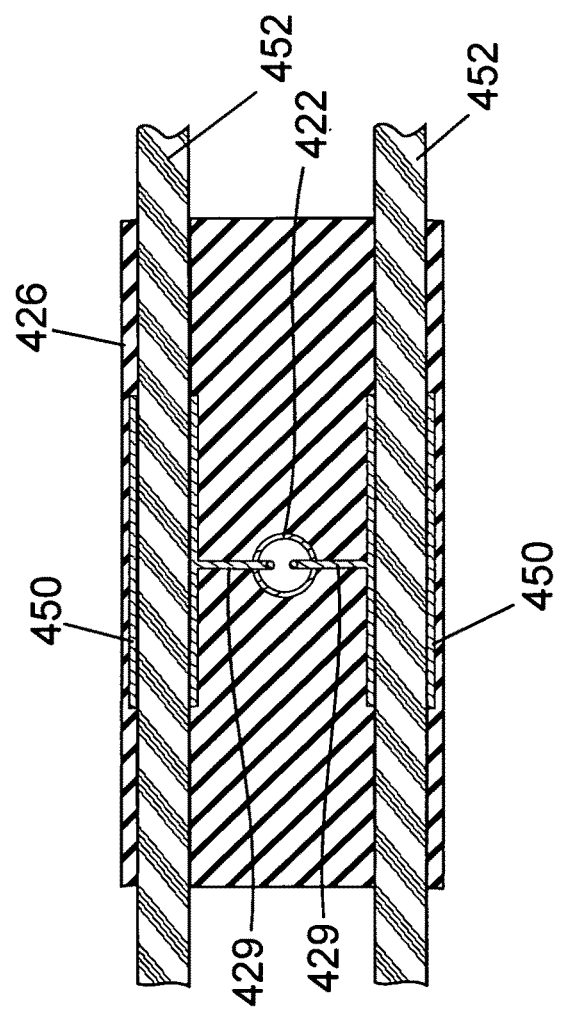

MODULAR LAMP HEAD AND ASSEMBLY FOR NON-DESTRUCTIVE TESTING

RELATED APPLICATIONS

This application is related to and claims priority from U.S. Provisional Patent Application 61/189,397 filed Aug. 19, 2008 and U.S. Provisional Patent Application 61/203,037 filed Dec. 17, 2008, the disclosures of which are both incorporated herein by reference in their entirety.

FIELD OF INVENTION

The present invention relates to lamps, and especially, but not exclusively, to a modular lamp for use in non-destructive testing.

BACKGROUND

Fluorescence is generally understood to be a property that enables certain materials to absorb light energy and radiate visible light at a longer wavelength than the absorbed light. Without being limited to any specific theory, it is widely accepted that electrons in fluorescent materials are excited upon being illuminated by light energy of a specific wavelength, and light energy of a longer wavelength is radiated from these materials as the electrons return to the unexcited or ground state. The specific excitation and radiation wavelengths are characteristics of particular fluorescent materials. The apparent brightness of a fluorescent material's luminescence is dependent, among other factors, on the wavelength emitted by the material and the intensity of the incident radiation that excites the material. A fluorescent material that has its excitation peak at a specific wavelength may quickly emit a much reduced luminescence as the wavelength of incident light deviates from the excitation peak. A fluorescent material will also lose the ability to fluoresce when the incident light does not have enough energy within the specific excitation range.

Lamps emitting radiation that excites fluorescence have been used for a wide variety of purposes, including, but not limited to, forensic inspection, readmission control, counterfeit currency detection, contamination inspection, non-destructive testing, and leak detection on equipment such as air conditioning and other fluid-containing systems. The lamp-light is commonly in the ultraviolet (UV) or in the visible blue-violet range, exciting a fluorescence somewhere in the visible range. The fluorescent material may be deliberately provided. For example, some banknotes have a fluorescent marker embedded in the paper and the UV light is used to detect the otherwise hidden marker. In another example, one method for detecting leaks in an air conditioning system is through the use of fluorescent dyes that are added to and mixed with the refrigerant in the system, with the combination of refrigerant and dye circulating through the air conditioning system. This method was first pioneered by Spectronics Corporation, the assignee of the present invention. In these leak detection systems, the dye circulates through the system, eventually seeping out at the source of the leak. When exposed to a suitable light source, such as an ultraviolet (UV) light, the dye fluoresces, thus highlighting the source of the leak. Ink that is visible only by fluorescence under an ultraviolet lamp can also be used in re-admission stamps at entertainment events.

The fluorescence may be an incidental property of some material that it is desired to detect, measure, or observe. For example, many biological materials, including rodent hair and urine, are naturally fluorescent. Other examples of the use of fluorescence include the detection of counterfeit currency and other documents. Many minerals, such as diamonds, can be recognized or distinguished by their levels and colors of natural fluorescence.

Many current fluorescence-exciting lamps emit light in long wave ultraviolet (UV-A) wavelength range of about 320 nm to about 400 nm, for example, around 365 nm, in the medium wave ultraviolet (UV-B) range from about 280 nm to about 320 nm, for example, around 315 nm, or in the short wave ultraviolet (UV-C) range, for example, around 254 nm, or in the visible violet/blue range from about 400 nm to about 480 nm within the electromagnetic spectrum.

Unfortunately, visible (including ambient) light competes with the fluorescence from dye for the attention of the person conducting the test. The visibility of the fluorescent response is increased when the intensity of other visible light is reduced, so that the fluorescent response is not masked or washed-out by other light. This is particularly true where the system has shiny surfaces that reflect visible or ambient light. Thus, ultraviolet lamps directed in otherwise dark conditions at a system containing a UV responsive fluorescent material may reveal the fluorescent material glowing against the dark background. When performed in total darkness, the outcome of such a procedure is often enhanced; however, total darkness is often not available in testing environments, such as an outdoor air conditioner where the sun cannot be shut off, or a shop floor where darkness may be dangerous when machinery in motion is involved.

Similarly, luminescent materials are also used in non-destructive testing. For example, fluorescent dyes combined with iron filings can be used to detect faults such as stress fractures. The combination of iron filings and fluorescent dye is attracted to the faults and, again, the dye emits visible light when illuminated by appropriate incident wavelength light. A very small fault is often difficult to detect even though such a small fault may present a potentially great danger. Thus, any assistance in identifying these faults would be beneficial.

Existing ultraviolet lamps have several weaknesses. Some concerns with existing ultraviolet lamps are their cost, size, and power consumption. For low power consumption and cost, fluorescent lamps can be used to generate the incident radiation. However, fluorescent lamps generate a low intensity of incident ultraviolet radiation. Because of this, it is desirable to be able to bring the lamp in close proximity to the fault. This is often difficult in the tight spaces available when working around machinery and equipment.

A hand-held UV lamp was developed by Spectronics Corporation and is described in U.S. Pat. No. 6,953,940, which is incorporated herein by reference in its entirety. That lamp is light and easily maneuverable. However, the small area of illumination generated by the lamp makes inspection of larger areas more time consuming. More particularly, the narrow width of the unit permits light from the surrounding environment to sometimes overpower the fluorescent response in brightly lit rooms, thus making detection difficult. The narrow width of light also has limited usage in the field of non-destructive testing where typically large areas are being tested for faults.

Halide lamps are currently in common use in non-destructive testing (NDT), but halide lamps get very hot and project light covering a wide wavelength. To accommodate for the wide wavelength coverage, expensive filters are used to remove the unneeded wavelengths of light and project the proper wavelength needed for testing. Since the filters are absorbing or reflecting light, they tend to heat up the ambient air surrounding the lamp.

A need, therefore, exists for a lamp head that is compact, emits ultraviolet (including blue wavelength) light with an effective intensity, and does not generate a large amount of heat.

SUMMARY OF THE INVENTION

The present invention is directed to a lamp module for use in non-destructive testing and inspection. The module includes a module body with front and rear ends, and a side wall that connects the front and rear ends. The module body includes a mounting chamber located within the side wall.

A plurality of light sources, preferably LEDs, are mounted within the chamber and oriented to so as to emit light out of the front end of the body. At least one light source emits light having a wavelength selected to produce fluorescence of an illuminated material. A fan is mounted to the body to dissipate heat generated by the light sources when the fan is activated. Electrical connectors extend out of the body and are electrically connected to the light sources and the fan for supplying current. The module can be installed in various structures or systems, including in a luminaire, an overhead light housing or a track light system.

The light emitting diodes are preferably mounted on a circuit board affixed to the base of the chamber. The electrical connectors include wire leads that are connected to wire conductors on the printed circuit board.

In one configuration there are four light emitting diodes mounted on the circuit board, one light emitting diode mounted so as to be substantially in the center of the chamber and the remaining three light emitting diodes being spaced radially outward from the center light emitting diode and substantially equidistant from each other. The center light emitting diode preferably emits light having a wavelength in the visible spectrum, and the remaining light emitting diodes emit light having a wavelength below 500 nm.

The module body may include one or more heat fins for dissipating heat from the light emitting diodes. The fan is preferable mounted to the housing so as to draw heat from the fins.

A switch is connected to the electrical connectors for controlling the supply of current to the light emitting diodes and the fan. the switch may be located distant from the module.

The lamp module may be mounted within a housing which includes a plurality of cavities. A module body is mounted within each cavity. In such a configuration, the housing may be mounted overhead to provide broad illumination.

In one embodiment, the module is part of a modular lamp system for non-destructive testing and inspection. A plurality of mounting bases are provided each adapted to be attached to a wall, ceiling or other support structure. Each base includes connectors for connecting the base to an adjacent base, and conductors for transmitting current from the adjacent base to the base. At least one support is attached to each base. The support has a first end that attaches to the base and a second end that attaches to a lamp module. Electrical conductors extend between the base and the lamp module. Each electrical conductor is attached to an electrical conductor in the base and to a conductor in the lamp module.

BRIEF DESCRIPTION OF DRAWINGS

For the purpose of illustrating the invention there is shown in the drawings various forms which are presently preferred; it being understood, however, that this invention is not limited to the precise arrangements and instrumentalities particularly shown.

FIG. 6 shows another embodiment of a lamp assembly in the form of a hand-held pistol grip lamp that incorporates the module of FIG. 4.

FIG. 7 shows a further embodiment of a lamp assembly in the form of a hand-held straight lamp that incorporates the module of FIG. 4.

FIG. 8 depicts one embodiment of the modular light assembly with a series of modular light units assembled into a system.

FIG. 9A is a side cross-sectional view of the base of FIG. 8.

FIG. 9B is a top cross-sectional view of the embodiment of the base of FIG. 9A.

FIG. 10A is a side cross-sectional view of an alternate embodiment of the base.

FIG. 10B is a top cross-sectional view of the embodiment of the base in FIG. 10A.

DETAILED DESCRIPTION

It will be appreciated by those skilled in the art that the present invention may be practiced in various forms and configurations. This detailed description of the disclosed embodiments is presented for purposes of clarity of understanding only, and no unnecessary limitations should be implied therefrom.

Figure 1:
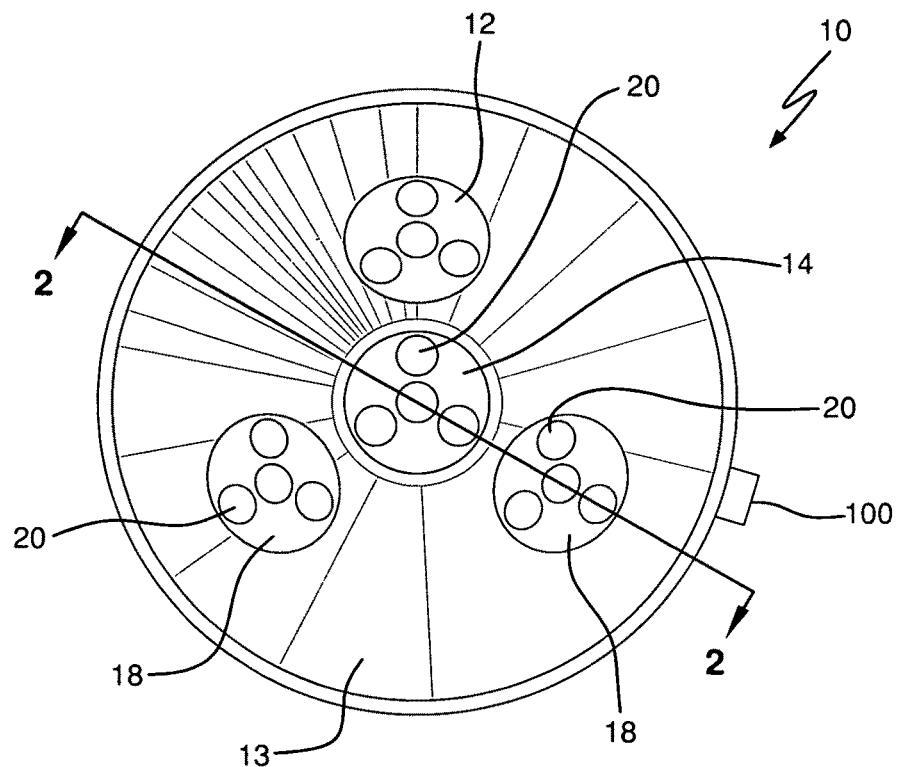
FIG. 1 shows a plan view of an embodiment of a lamp assembly of the present invention.

Referring to FIG. 1, one embodiment of a lamp or lamp assembly 10 is shown which includes a plurality of modular heads or modules 12 mounted in a housing 13, each module including at least one light-emitting diode (LED). In one embodiment, the lamp assembly preferably includes a central module 14 containing at least one white LED 20 emitting full or substantially full spectrum (white) light. One or more peripheral modules 18 are oriented around the central module. In one embodiment, the lamp preferably includes three peripheral modules arranged in a triangular pattern around the central module; however, one of ordinary skill in the art will realize that the peripheral modules need not be limited in number or arrangement. The peripheral modules each include at least one non-white LED and, preferably at least one white LED. The non-white LEDs preferably emit light having a wavelength in the ultraviolet (UV) or blue range. More preferably, the UV/blue LEDs preferably emit light with a wavelength between about 254 nm and about 500 nanometers. In one embodiment, the LEDs are UV LEDS manufactured by Nichia with a range of between about 360 nm to about 370 nm with a peak at approximately 365 nm. As will be discussed in more detail below, each LED also includes a reflective surface 17, as more readily seen in FIG. 3. For simplicity, the non-white LEDs are referred to herein as UV LEDS, however it should be readily apparent that the LEDS can be selected to emit any desired color.

The LEDs are chosen to have a spectral output optimized for the intended use of the lamp. For example, where the lamp is intended as an inspection lamp for fluorescence leak detection, the LEDs in the particular modules may be selected to emit light strongly at the excitation frequency of a fluorescent dye, or in a range including the excitation frequencies of a range of fluorescent dyes, typically in the blue, violet, near ultraviolet and ultraviolet range, such as UV-A, UV-B or UV-C ranges, of the spectrum.

Figure 2:
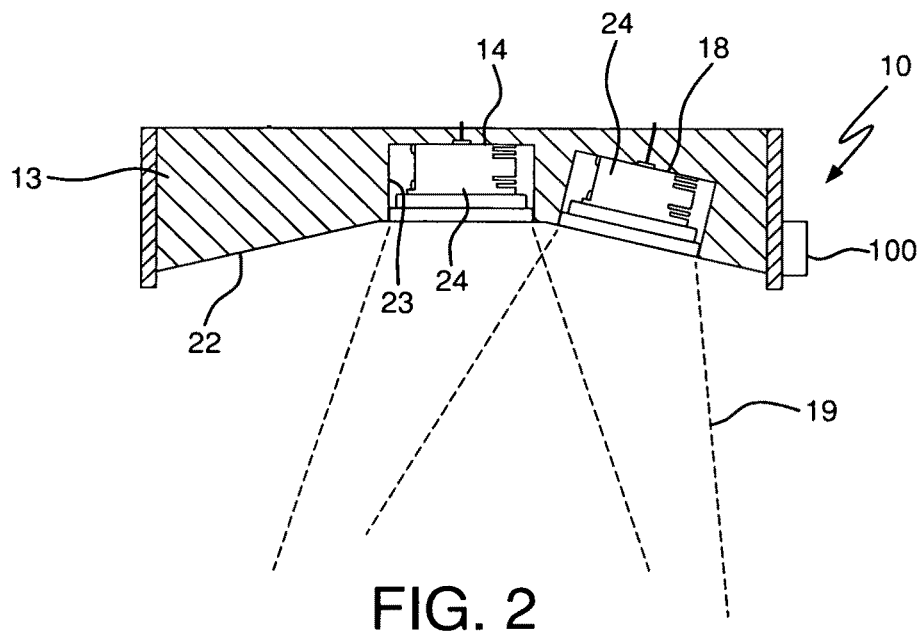
FIG. 2 shows a cross section of the lamp assembly shown in FIG. 1.

In one intended use of the invention, the modules are incorporated into an overhead lamp assembly for illuminating downwardly over a large viewing area, such as onto a table surface. FIGS. 1 and 2 generally illustrate such as assembly 10. The lamp assembly includes multiple modular heads 14, 18 mounted into the housing 13 so as to emit light in the desired direction. As seen in FIG. 2, the housing 13 preferably includes a concave or frustoconical bottom surface 22 with recesses or cavities 23 into which the modules 14, 18 are mounted and from which the LED light can emit. The modules may be mounted in the housing in an adjustable manner so that the angle of each module may be adjusted to differ from the angle of the housing surface, thereby adjusting the illumination provided by each module. In a preferred embodiment, the modules or recesses 23 into which the modules are mounted are oriented so that the pattern of emitted light 19 illuminates a defined area below the light, such as is shown in FIG. 2.

Figure 3:
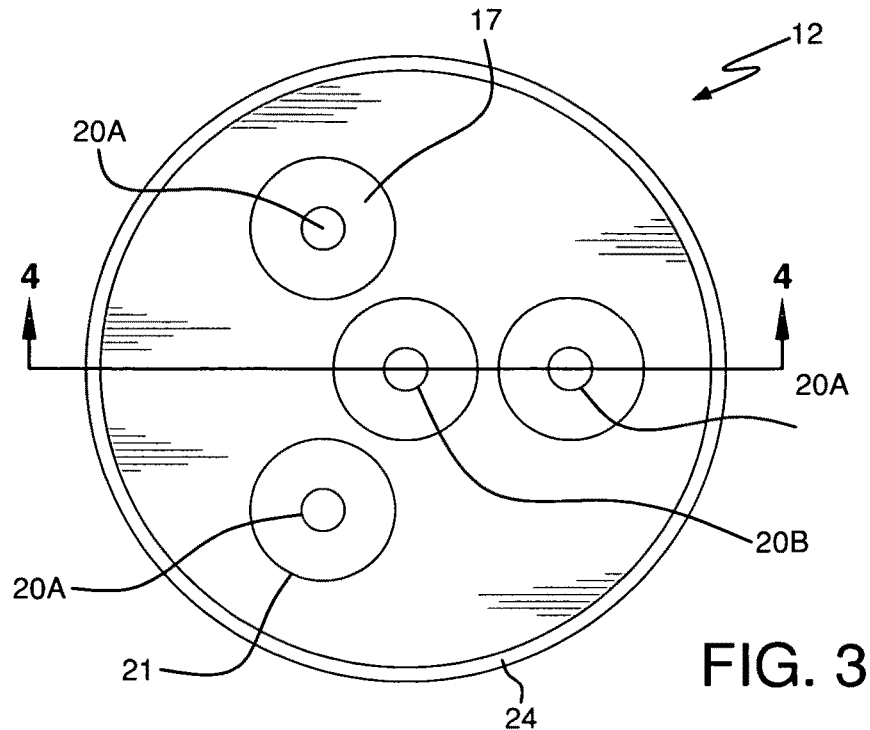
FIG. 3 shows a plan view of a module lamp head of the assembly shown in FIG. 1
Figure 4:
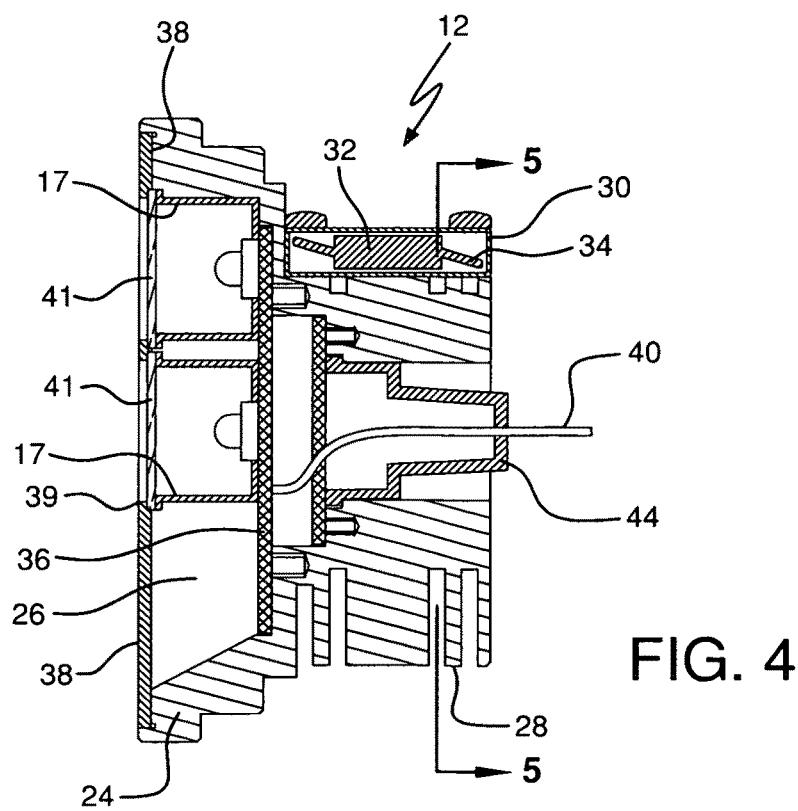
FIG. 4 shows a cross section of the module shown in FIG. 3 taken along lines 4-4.
Figure 5:
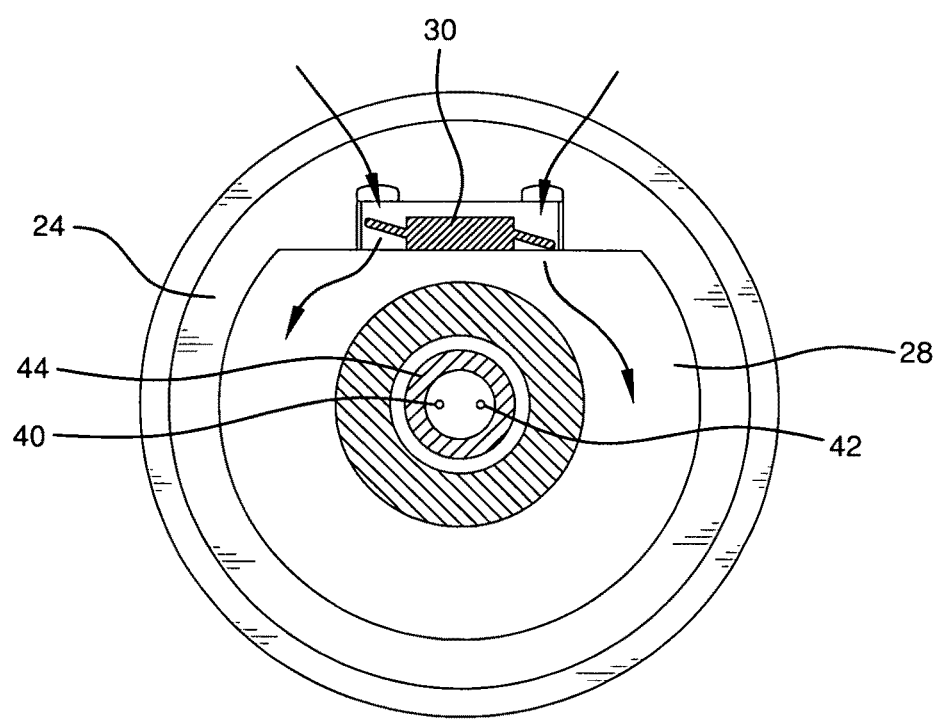
FIG. 5 shows a cross section of the module of FIG. 4 taken along lines 5-5.

FIGS. 3, 4, and 5 show a preferred form of the module 12. The LEDs in this embodiment may be white LEDs 16 or non-white LEDs 20 or mix thereof, as the preferred arrangement is not dependent on LED color. The module includes a module body 24 which has at least one mounting chamber 26 in which the LEDs are located, and cooling fins 28, which help dissipate the heat generated by the LEDs.

As shown in FIGS. 3 and 4, each module 12 preferably includes a plurality of LEDs 20, for example, four as in the illustrated embodiment, mounted to the body 24 and arranged in a pattern. More particularly, the LEDs are mounted within the mounting chamber 26, preferably on a printed circuit board 36 mounted to the bottom of the mounting chamber 26. In the illustrated embodiment, three of the LEDs 20A each emit non-white light. Preferably, the non-white LEDs are UV LEDs for facilitating non-destructive fluorescent inspection. The fourth LED, preferably located in the center of the module, includes at least one white LED 20B, for facilitating general (visible light) viewing. In one embodiment of the invention, the LEDs have a wattage of between 1 and 3 watts. It is contemplated that wattages greater than 3 watts can be used.

A tapered reflector 17 with a reflective surface 17 may be mounted within the chamber and positioned around each LED to aid in reflecting the light from the LED in a direction out of the lamp module. The reflective surface helps to focus the light from the LEDs while at the same time minimizing loss of light due to absorption of the light waves by the chamber. The reflector can be made from any reflective material such as mirrors, glass, reflective metals, reflective plastics (such as a white plastic), wherein each case the reflective surface is the surface of the material forming the reflector, or made from a non-reflective material with a reflective coating applied to it. While the preceding discussion refers to the lamp as including individual reflectors, it is also contemplated that the LEDs may simply be mounted on the PCB board and the mounting chamber 26 may include reflective walls. It is contemplated that each module body 24 can include more than one LED 20 in a reflector.

In one preferred embodiment, the reflector is an LED housing that is preferably attached to the printed circuit board. The LED housing includes an opening in the bottom through which the LED protrudes. One suitable LED housing is the NIS033U Smooth Spot sold by Ledil Oy, Salo Finland. The LED housing may include an integral lens made from polymer material for providing high transmission of UV light. The lens and housing combine to provide a smooth beam of light.

If reflectors are not used, that to further assist in transmitting the light, the modules can be in various orientations that allow the light to be reflected away from the chambers. For example, the chambers can have a concave shape.

The LEDs are preferably operable by a switch (generally depicted in FIG. 1 by the numeral 100) such that an operator may illuminate the central module and the peripheral modules either simultaneously or separately. The switch can be configured to allow the user to select the illumination desired or the circuitry can be arranged to cycle through all the different groups of LEDs upon depressing or activating the switch. Thus, the lamp could emit some or all of these wavelengths. Also, combinations of any of the LEDs can also be illuminated. The switch may, alternatively, be placed in connection with an individual module, allowing each module to be operated independently, and allowing a module to be easily removed or replaced, or placed in another fixture. The switch is arranged to control a circuit that connects to leads 40 and 42 (FIG. 5) from the module, allowing the circuit to operate the LEDs through various stages. Starting in an "off" position (i.e., no power is provided to any of the modules shown in FIGS. 1 and 3), operating the switch once takes the circuit into a first stage. In the first stage, power is provided to the three non-white LEDs 20A in a module. In a second stage, which is achieved by operating the switch a second time, the circuit is returned to the "off" position. In a third stage, which is achieved by operating the switch a third time, power is provided to the white LEDs 20B. Operating the switch a fourth time, the circuit is returned to the "off" position, with no power being supplied to the LEDs. The switch may be any conventional switch including a pushbutton, toggle or dial.

Other variations of the staging are also within the scope of the invention. For example, as discussed above, in FIG. 1 a lamp assembly is shown where the individual modules 12 could be designed to operate to emit a single color, the center module emitting white light while the peripheral modules emit UV light. Thus, the switch 100 could be configured to control the supply of power to different modules, depending on the desired light to be emitted.

As discussed above, one of the problems with LEDs has been the degradation of the electrical components from heat buildup. Theoretically, an LED should have a very long lifespan. However, in actual use, the heat from the LED tends to breakdown the electrical components, shortening the life of the LED. This problem is enhanced when more than one LED is mounted in a lamp head, or when the LED is a high wattage bulb (such a 1 watt). To reduce the heat, the present invention incorporates a fan into the module. More particularly, a fan enclosure 30, which contains a fan 32 is mounted to the module body 24. The fan is preferably mounted on the side of the body and arranged so as to remove heat from the body 24. Testing has shown that the incorporation of a fan into the module has reduced the temperature of the module body by approximately 30 degrees Celsius—from approximately 80-90 degrees Celsius to approximately 50-60 degrees Celsius.

The fan can remove heat by either drawing air away from between the fins 28 or, as is shown in the figures, force air to flow between the fins 28, causing the air to flow across the cooling fins and out through vents in the housing. It is preferable to force cool ambient air toward the fins, as is illustrated by the arrows in FIG. 5.

As seen in FIG. 4, the chamber 26 also includes a front cover 38. The front cover 38 includes apertures or holes 39 for permitting the light from the LEDs to pass through. As discussed above, the preferred embodiment of the invention uses LED housings with an attached lens over the end of the housing. The lens assists in focusing the light out through the apertures. If the LED housing does not include a lens, then at least one transparent or translucent window is mounted to the cover 38 to protect the LEDS. The window is preferably made from a durable material so that the LEDs are protected, but the light emitted from the LEDs is not impeded. For example, a window can be made from plexiglass, glass, and other similar materials. Alternatively, the cover 38 may include multiple holes 39 with individual windows 41 mounted so as to cover the holes 39. It is also contemplated that the window may be a lens to focus the light emitted from the LEDs.

As discussed above, the LEDs are preferably mounted to printed circuit board 36 which, in turn, is mounted about its periphery to the body 24. The mounting can be through any conventional means. As heat from the LEDs develops inside the chamber 26, it is conducted through the body toward the rear where the radial cooling fins are located. The LEDs are mounted to a heat sink pad on the circuit board. The heat sink pad conveys heat from the LEDs directly into the circuit board and from there into the body 24. Since the interfaces between the various components making up the module include irregularities, heat conduction is somewhat diminished. As such, a conductive coating may be added between at least the printed circuit board 36 and the body 24, and, more preferably, between any components through which a significant portion of the heat is to pass. The coating may be a powder-based coating that serves to facilitate heat transfer by filling in the tiny air gaps that exists between components of the module. The elimination of these air gaps, along with the conductive properties of the coating, helps transfer heat generated by the LEDs through the module body to the cooling fins. The channeling of the heat away from the cover 38 and the LEDs helps protect the components of the module, as well as allowing for more efficient dispersion of the heat.

As shown, the module 12 is preferably designed to plug into any desired housing, including an over head luminaire or handheld housing with suitable connections to engage with and support power through the leads 40 and 42. FIGS. 6 and 7 illustrate the incorporation of the module 12 into a handheld pistol grip lamp housing 200 and a handheld straight lamp housing 300. The housings include vents 210, 310 to assist in heat dissipation. A mounting ring 220, 320 may be used to secure the module 12 into the housings 200, 300 by engaging with threads or similar mounting attachments.

Referring to FIGS. 8-10B, a modular nondestructive testing lighting system 400 is shown according to one preferred embodiment. The lighting system 400 preferably includes a plurality of individual lighting units 412 designed to connect to one another and to a power supply 414. Each lighting unit 412 includes at least one lamp head 416 with a housing or body 418 which contains one or more lamps 420. The lamps 420 are configured to emit light in at least a wavelength operable for permitting nondestructive testing (NDT) of a component. Preferably the lamps 420 emit light in the UV or blue wavelengths (i.e., below about 500 mm) which are useful in exciting fluorescent materials, such as dyes, causing them to fluoresce and thereby indicating a location of interest, such as a crack or leak location. The lamp may be any suitable light producing source, such as a laser diode, halogen bulb, or, more preferably, a light emitting diode (LED). Preferably the lamp head 416 is one of the lamp modules 12 described above.

The lamp head 416 is preferably attached to one end of an elongated support 422. An opposite end of the support is attached to a base 424. The attachment of the support 422 to the lamp head 416 and the base 424 may be fixed or, more preferably, may be adjustable, such as pivotable, extendible, or rotatable, so as to permit movement of the lamp head 416 relative to the base 424. It is also contemplated that the lamp head may be movable on the support 422 so that the lamp head 416 can be translated, such as by sliding, along the length of the shaft 422 to a desired position. A set screw or other locking feature may be used to temporarily fix the location of the lamp head 416 along the support 422.

The support 422 positions the lamp head 416 at a location spaced apart from the base 424. The support 422 may be a rigid or fixed length structure, such as one or more shafts that may house electrical wiring for transmitting current between the base 424 and the lamp 420. Alternatively, the support may be adjustable so as to permit variation in the location of the lamp head relative to the base. For example, the support 422 may include an intermediate hinge which permits folding of the support to adjust the location of the lamp head 416. The support 422 may, alternately, be flexible (e.g., bendable) so as to permit a multitude of positional adjustments of the lamp head 416. Still further, the support 422 may include telescoping sections that permit extension of the lamp head 422 to a desired location. It is contemplated that the base 424 includes mounting holes for securing the base to a ceiling. In such a ceiling mounted configuration, the support 422 may be a cord hanging from the base or a cord reel mounted to a base and from which the lamp heads hang down.

Referring to FIGS. 9A and 9B, in one embodiment, the base 424 includes a base housing 426 which, in one embodiment, includes two electrical connectors or prongs 428 protruding out of one side. The prongs 428 are connected to electrical wiring or conductors 429 in the housing 426 that, in turn, connect to the wiring or conductors 431 in the support 422 that lead to the lamp 420. Two sockets or receptacles 430 are also preferably formed on the opposite side of the housing prongs 428. The receptacles 430 are sized to receive prongs 428 of a mating lighting unit 412. Each receptacle 430 includes an electrical contact that connects one of the wires or electrical conductors 429 inside the housing 426 that leads to an electrical contact on a prong 428. In this embodiment, multiple lighting units can be connected to one another by plugging the prongs 428 on one lighting unit into the receptacles 430 on the other lighting unit 412. A switch (not shown) may be included that permits control of the transmission of current along the power cord.

The end lighting unit in a series of units is connected to the power source 414 through a power cord 432. The power cord 432 includes a connector at one end and a receptacle at the other end configured to engage with prongs 428 on a lighting unit 412. Alternatively, one lighting unit can be configured as an end unit and be hard wired to a power cord 432.

It is also contemplated that connector cords (not shown) can be used to space apart adjacent lighting units. The connector cords each include a set of prongs 428 on one end for connecting with receptacles 430 on a lighting unit 412, and a set of receptacles on the other end that connect with a set of prongs 428 from a distant lighting unit 412. The connector cord may be of fixed length or, more preferably, is flexible between its prong end and receptacle end.

In one embodiment of the invention (not shown), the lighting unit includes a third electrical conductor that extends through the support 422 to the lamp head. The electrical conductor is connected to a switch in the lamp head 416. Wire leads from the switch connect to two different lamps or light sources. At least one lamp emits light having a wavelength useful for NDT inspection (e.g., below 500 nm). Preferably at least one other lamp emits visible light, such as white light. It is also contemplated that lamp heads with light sources having multiple inspection wavelengths could also be used (e.g., blue, ultraviolet, red, etc.) The switch controls which of the wire leads current is supplied along so as to activate the desired light source, thus permitting the light that is emitted from the lamp head to be switched between an NDT light source and a visible (white) light source or between different NDT light sources. The third electrical conductor in the support 422 would connect through the housing to a third electrical prong (or receptacle) that connects with a third receptacle (or prong) on a mating unit and/or the power cord. The additional wire conductor in the power cord would connect with a control switch for permitting the user to control when signals are provided on the third connector.

FIGS. 10A and 10B illustrate an alternate embodiment of the invention. In this embodiment, the housing 426 does not include prongs and receptacles. Instead, the housing 426 includes two through holes which have housing contacts 450 mounted on an inside surface of the holes. The housing contacts connect to the internal wiring 429 which then connect with the wires 431 in the support 422. Two continuous power conductors extend through the holes and are in contact with the housing contacts so as to pass current therebetween. In this embodiment, housings 426 for any number of units 412 are slid onto the conducts 452.

It is also possible to create a track using connectors to attach bases together. For example, track lighting connectors are available from many companies, such as Wei Hui Enterprises Co. Ltd., Taipei Hsien, Taiwan R.O.C., that can be attached to bases and which include suitable wiring for transmitting power to the lamps. The track can be formed in a variety of configurations to meet the environmental limitations imposed on the lighting system. A sample of suitable connectors are shown on www.cens.com/ishow/w/wenhui/pro3.htm.

Figure 11:
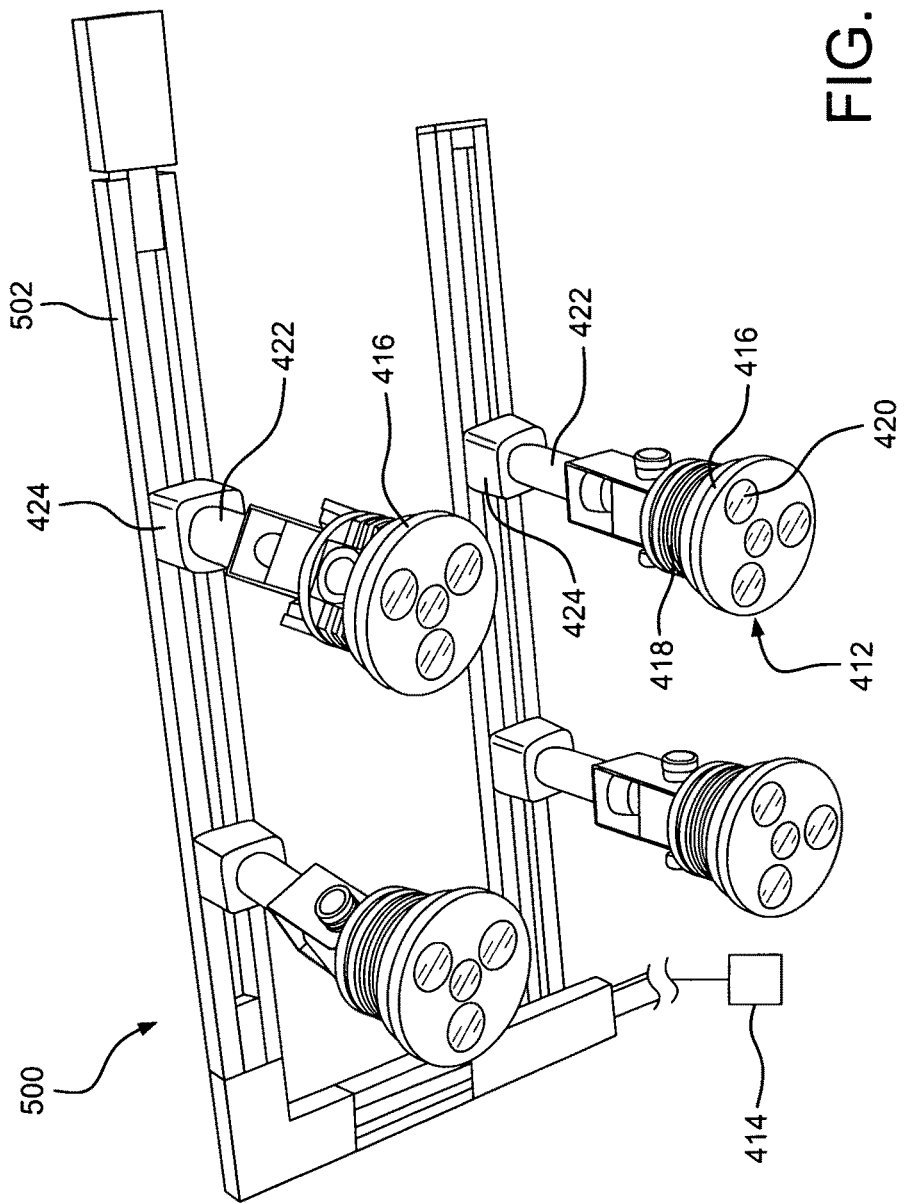
FIG. 11 depicts an embodiment of a modular light track assembly with a series of modular light units mounted onto a track.

FIG. 11 illustrates one preferred configuration of a track assembly 500. The assembly includes a track 502 which includes conductors (not shown) for transmitting current from a power source 414 to the light sources 420 in the lamp heads 416. In this embodiment, each base 424 is designed to slide along the track 502 to any desired location. The attachment of the base to the track can be similar to a dovetail engagement with each side of the track including a conductor. Thus, the arrangement illustrated permits positioning of lamp heads at various locations along a track. the track can be segmented so that various track arrangements can be achieved by attaching desired segments together.

Various embodiments of this invention are described herein. However, it should be understood that the illustrated embodiments are exemplary only, and should not be taken as limiting the scope of the invention.

We claim:

1. A lamp module for use in non-destructive testing and inspection, the module adapted to emit light having a wavelength selected to produce fluorescence of an illuminated material to facilitate nondestructive testing and inspection of a component or item, the lamp module comprising:
    a module body including a front end, a rear end, and a side wall between the front and rear ends, the module body including a mounting chamber located within the side walls proximate to the front end, the chamber including a base opposite from the front, end;
    a plurality of light emitting diodes mounted within the chamber and oriented to so as to emit light out of the front end of the body, at least one of the light emitting diodes emitting light having a wavelength selected to produce fluorescence of an illuminated material, the light emitting diodes being thermally coupled to the module body;
    cooling fins formed integral with and extending radially outward from at least a portion of the side wall of the module body and having surfaces oriented substantially parallel to a plane defined by the front end of the module body, the fins on one side of the body being shorter than on the other so as to form a mounting surface on the radial outer ends of the fins which is located at least partly below the chamber;
    a fan mounted to the mounting surface of the fins and oriented so that blades of the fan generate a flow of air along the surfaces of the fins and around the periphery of the sidewall when the fan is activated to facilitate the dissipation of heat generated by the light emitting diodes, the fan having an inner side mounted to the mounting surface and an outer side facing away from the fins; and
    electrical connectors extending out of or on a surface of the module body and electrically connected to the light emitting diodes and the fan for supplying current to the diodes and fan.

2. The lamp module according to claim 1 wherein the light emitting diodes are mounted on a circuit board affixed to the base of the chamber, the base of the chamber contacting the sidewalks, of the module body, thereby thermally coupling the light emitting diodes to the module body, and
    wherein the electrical connectors include wire leads that are, connected to wire conductors on the printed circuit board.

3. The lamp module according to claim 2 wherein there are four light emitting diodes mounted on the circuit board, one light emitting diode mounted so as to be substantially in the center of the chamber and the remaining three light emitting diodes being spaced radially outward from the center light emitting diode and substantially equidistant from each other, the center light emitting diode configured to emit light having a wavelength in the visible spectrum, and the remaining light emitting diodes configured to emit light having a wavelength below 500 nm.

4. The lamp module according to claim 3 further comprising a reflector mounted within the chamber and having a reflective surface, the reflector positioned so that the reflective surface substantially surrounds the sides of at least one of the light emitting diodes and extends substantially from the light emitting diode to the front end of the module body; and
    a lens extending substantially across the front end, the lens being made from a material that permits transmission of at least a portion of the light emitted from the light emitting diodes in the chamber.

5. The lamp module according to claim 1 further comprising a switch connected to the electrical connectors for controlling the supply of current to the light emitting diodes and the fan.

6. The lamp module according to claim 5 wherein the switch is located distant from the module.

7. The lamp module according to claim 1 further comprising a heat sink mounted in the module body near or on a portion of the printed circuit board for conveying heat from the light emitting diodes away from the diodes and toward the fins.

8. The lamp module according to claim 1 further comprising a conductive coating on at least a portion of the module body for facilitating conduction of heat into the body.

9. The lamp module according to claim 6 further comprising a housing which includes a cavity, the module body being mounted within the cavity, the housing having a compartment for storing batteries, wherein the connectors on the module and the switch are electrically connected to the battery compartment for receiving current from batteries, and wherein the switch is mounted on the housing.

10. The lamp module according to claim 6 further comprising a housing which includes a plurality of cavities, wherein a module body is mounted within each cavity, the housing being connectable to an external power source, the connectors on the module and the switch being connected to the power source through the housing for receiving current from power source.

11. A modular lamp system for non-destructive testing and inspection comprising:
    a plurality of lamp modules according to claim 1;
    a plurality of mounting bases each adapted to be attached to a wall, ceiling or other support structure, each base including connectors for connecting the base to an adjacent base, and conductors for transmitting current from the adjacent base to the base;
    at least one support attached to each base, the support having a first end that attaches to the base and a second end that attaches to the lamp module; and
    electrical conductors extending between the base and the lamp module: each electrical conductor being attached to an electrical conductor in the base and to a conductor in the lamp module.

12. The modular lamp system according to claim 11 further comprising a switch located between the connectors in the base and a power source, the switch adapted to control the supply of current to the light emitting diodes and fan in the lamp module.

13. The modular lamp system according to claim 12 wherein the attachment of the lamp module to the support is configured to permit relative movement between the lamp module and the support for permitting change in the direction that the light emitted is emitted from the lamp module.

14. A lamp module for use in non-destructive testing and inspection, the module adapted to emit light having a wavelength selected to produce fluorescence of an illuminated material to facilitate nondestructive testing and inspection, the lamp module comprising:
    a housing;
    at least one LED module mounted within the housing, the LED module including:
    a body having an open end and at least one mounting chamber formed in the body at the open end;
    a plurality of light emitting diodes mounted within the chamber and oriented to emit light out of the open end of the chamber, at least one of the light emitting diodes emitting light having a wavelength selected to produce fluorescence of an illuminated material, the light emitting diodes being thermally coupled to the module body;
    cooling fins formed integral with and extending radially outward from a side of the body and having surfaces oriented substantially parallel to a plane defined by the open end of the body, the fins on one side of the body being shorter than on the other so as to form a mounting surface on the radial outer ends of the fins which is located at least partly below the chamber;
    a fan mounted to the mounting surface of the fins and oriented so that blades of the fan generate a flow of air along the surfaces of the fins and around the periphery of the sidewall when the fan is activated to facilitate the dissipation of heat generated by the light emitting diodes, the fan having an inner side mounted to the mounting surface and an outer side facing away from the fins;
    electrical leads extending out of or on a surface of the body and electrically connected to the light emitting diodes; and
    a switch in the housing connected to the leads for controlling the light emitting diodes and the fan in the module.

15. The lamp assembly of claim 14, wherein the housing includes multiple LED modules arranged about one surface of the housing so as to emit light generally toward a common location; wherein one of the modules is configured to emit at least white light.

16. The lamp assembly of claim 14, wherein the cooling fins are positioned on a portion of the body on the opposite side of the chamber from the open end.

17. The lamp assembly of claim 16, wherein at least one of the light emitting diodes is located in the center d the chamber and emits visible light, and wherein there are at least two other light emitting diodes mounted within the chamber and emit ultraviolet or blue light.

18. The lamp assembly of claim 17, wherein the light emitting diodes are mounted to a printed circuit board attached a bottom surface of the chamber, the bottom surface of the chamber contacting the body thereby thermally coupling the light emitting diodes to the body; and
    wherein the reflective surface is a plurality of reflectors, one reflector associated with each light emitting diode, the module including a cover mounted over the open end and having at least one window for transmitting light out of the chamber, the reflectors being mounted to the cover.

19. The lamp assembly of claim 14, wherein each of the LED module can be detached from the housing.

20. The lamp assembly of claim 18, wherein a conductive coating is disposed between a portion of the printed circuit board and the body, the conductive coating adapted to facilitate the transfer of thermal energy from the printed circuit board to the body.

21. A modular lamp system for non-destructive testing and inspection comprising:
    a plurality of lamp modules, at least some of the modules adapted to emit light having a wavelength below 500 nm for producing fluorescence of an illuminated material to facilitate nondestructive testing and inspection of a component or item, each lamp module including:
    a module body including a front end, a rear end, and a side wall between the front and rear ends, the module body including a mounting chamber located within the side walls proximate to the front end, the chamber including a base opposite from the front end;
    a plurality of light sources mounted within the chamber and oriented to so as to emit light out of the front end of the body, at least one of the light sources emitting light having a wavelength below 500 nm to produce fluorescence of an illuminated material; the light emitting diodes being thermally coupled to the main body;
    cooling fins formed integral with and extending radially outward from the at least a portion of the side wall of the module body and having surfaces oriented substantially parallel to a plane defined by the front end of the module body, the fins on one side of the body being shorter than on the other so as to form a mounting surface on the radial outer ends of the fins which is located at least partly below the chamber;
    a fan mounted to the mounting surface of the fins and oriented so that blades of the fan generate a flow of air along the surface of the fin and around the periphery of the sidewall when the fan is activated to facilitate the dissipation of heat generated by the light sources, the fan having an inner side mounted to the mounting surface and an outer side facing away from the fins;

electrical connectors extending out of or on a surface of the module body and electrically connected to the light sources and the fan for supplying current to the light sources and fan;

a plurality of mounting bases each adapted to be attached to a wall, ceiling or other support structure, each base including connectors for connecting the base to an adjacent base, and conductors for transmitting current from the adjacent base to the base;

at least one support attached to each base, the support having a first end that attaches to the base and a second end that attaches to one of the lamp modules for supporting the module spaced apart from the base; and electrical conductors extending between each base and its lamp module; each electrical conductor being attached to an electrical conductor in the base and to a conductor in the lamp module.

22. The modular lamp system according to claim 21 wherein the attachment of the lamp module to the support is configured to permit relative movement between the lamp module and the support for permitting change in the direction that the light emitted is emitted from the lamp module.

* * * * *